United States Patent [19]

Iijima et al.

[11] 4,132,678

[45] Jan. 2, 1979

[54] TRANSPARENT LIQUID SHAMPOO

[75] Inventors: Eiji Iijima, Sakura; Hiroshi Watanabe, Funabashi; Shizuo Hayashi, Sugito, all of Japan

[73] Assignee: Kao Soap Co., Ltd., Tokyo, Japan

[21] Appl. No.: 720,988

[22] Filed: Sep. 7, 1976

[30] Foreign Application Priority Data

Sep. 16, 1975 [JP] Japan .................. 50/111859

[51] Int. Cl.² .................. C11D 1/65; C11D 1/14; C11D 1/62
[52] U.S. Cl. .................. 252/545; 252/547; 252/548; 252/551
[58] Field of Search .......... 252/532, 545, 547, 551, 252/548; 424/326

[56] References Cited

U.S. PATENT DOCUMENTS

| | | | |
|---|---|---|---|
| 2,941,950 | 6/1960 | Korpi et al. .................. | 252/153 |
| 2,950,255 | 8/1960 | Goff .................. | 252/547 X |
| 3,086,943 | 4/1963 | Lang .................. | 252/547 X |
| 3,711,414 | 1/1973 | Hewitt .................. | 252/118 |
| 3,775,349 | 11/1973 | Tuvell et al. .................. | 252/547 |

FOREIGN PATENT DOCUMENTS 1249433 9/1967 Fed. Rep. of Germany.
1232698 5/1971 United Kingdom.
1261231 1/1972 United Kingdom.

OTHER PUBLICATIONS

Gohlke et al., "Alkyl Ether Sulfates Use in Growing in Liquid Detergents", Soap and Chemical Specialties, Oct., 1967, pp. 47-49, 62, 113, 186.
Gohlke et al., (II), "Alkyl Ether Sulfates in Liquid Detergents", Soap and Chemical Specialties, Mar., 1968, pp. 60, 62, 64, 66, 68, 146, 148.

*Primary Examiner*—P.E. Willis, Jr.
*Attorney, Agent, or Firm*—Blanchard, Flynn, Thiel, Boutell & Tanis

[57] ABSTRACT

A shampoo composition comprising, as critical components,
(A) from about 10 to about 40% by weight of an anionic surface active agent having the formula (I):

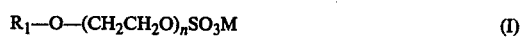

wherein $R_1$ is alkyl having 10 to 18 carbon atoms, n is the average mole number of added ethylene oxide units and is in the range of from 1 to 5 on the average, with the proviso that the content of compounds in which n = 0 is not higher than 5%, and M is an alkali metal or an organic amine, and (B) from about 0.1 to about 5% by weight of a cationic surfactant having the formula (II):

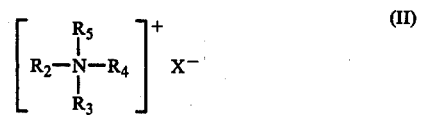

wherein $R_2$ is alkyl having 16 to 22 carbon atoms, $R_3$ and $R_4$ are alkyls having 1 or 2 carbon atoms, $R_5$ is alkyl having 1 or 2 carbon atoms or benzyl, and X is an anionic group.

5 Claims, No Drawings

TRANSPARENT LIQUID SHAMPOO

BACKGROUND OF THE INVENTION

1. Field of the Invention

The present invention relates to a transparent liquid shampoo composition. More particularly, the invention relates to a transparent liquid shampoo that imparts a good finish to washed hair.

2. Description of the Prior Art

Shampoos have previously been prepared by using as a main component an anionic surface active agent such as a sodium alkyl sulfate, a triethanolamine alkyl sulfate, a sodium or triethanolamine salt of a polyoxyethylene alkyl ether sulfuric acid ester, a potassium salt of a higher fatty acid, a triethanolamine salt of a higher fatty acid or a sodium alkyloyl taurine, and incorporating into such anionic surface active agent a foaming enhancing agent such as a higher fatty acid alkanolamide.

It is considered necessary that shampoos possess a good foaming property, a good detergency and a property of imparting a supple and soft finish to washed hair. In connection with the foaming property and the detergency, these properties can easily be obtained by appropriately selecting the kind and concentration of the anionic surface active agent and the kind and the concentration of the higher fatty acid alkanolamide. However, attempts to impart suppleness and softness to washed hair have not been completely satisfactory.

It has been attempted to incorporate liquid paraffin, a higher alcohol, an ester, other oils or fats, an amphoteric surface active agent, a cationic surface active agent or the like into an anionic surface active agent shampoo base in order to impart a supple and soft finish to washed hair. However, since the primary purpose of a shampoo is to wash away contaminants (mainly composed of oils and fats) on the hair and head skin, it is substantially impossible to cause oil and fat components of the shampoo to remain in the hair after washing, and even if some amount of them is left, the amount is very small and it exerts little, if any, effect of rendering washed hair supple and manageable.

It has also been attempted to incorporate an amphoteric surface active agent or a cationic surface active agent into an aqueous solution of an anionic surface active agent. However, it is difficult to obtain a transparent composition, and even if the additive is dissolved at a high temperature, crystals are precipitated when the composition is cooled to a low temperature. Accordingly, a transparent liquid shampoo having an acceptable commercial value cannot be obtained. In order to increase the water solubility of the amphoteric or cationic surface active agent for overcoming the above disadvantage, it has been attempted to shorten the length of the alkyl chain, or to use an ethylene oxide adduct derivative or to introduce two quaternary ammonium nitrogen atoms into the molecule. However, enhancement of the water solubility of the amphoteric or cationic surface active agent results in a considerable reduction of the hair-softening effect. Accordingly, even if a transparent shampoo is obtained by using such a modified surface active agent, the shampoo does not exert an acceptable effect of softening hair and rendering same supple and manageable.

SUMMARY OF THE INVENTION

We have discovered that when a specific cationic surface active agent having an excellent effect of rendering hair supple, is dissolved in a specific anionic surface active agent, there is obtained a shampoo capable of giving a good supple finish to washed hair and this solution is transparent and has a good stability at low temperatures.

More specifically, in accordance with the present invention, there is provided a shampoo composition comprising, as critical components (A) from about 10 to about 40%, preferably 13 to 25%, by weight of an anionic surface active agent having the formula (I):

$$R_1-O-(CH_2CH_2O)_n SO_3 M \qquad (I)$$

wherein $R_1$ is alkyl having 10 to 18, preferably 12 to 14, carbon atoms, n is the average mole number of added ethylene oxide units and is in the range of from 1 to 5 on the average, preferably 2 to 4, with the proviso that the content of compounds in which $n = 0$ is not higher than 5%, preferably less than about 4%, and M is an alkali metal such as sodium and potassium or an organic amine such as mono-, di- or tri-ethanolamine, and (B) from about 0.1 to about 5%, preferably, 0.3 to 3%, by weight of a cationic surface active agent having the formula (II):

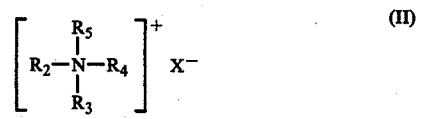

$$\begin{bmatrix} R_5 \\ | \\ R_2-N-R_4 \\ | \\ R_3 \end{bmatrix}^+ X^- \qquad (II)$$

wherein $R_2$ is alkyl group having 16 to 22 carbon atoms, $R_3$ and $R_4$ are alkyls having 1 or 2 carbon atoms, preferably methyl, $R_5$ is alkyl having 1 to 2 carbon atoms, preferably methyl, or benzyl, and X is an anionic group such as a halogen atom, e.g., Cl, Br or I, or a monoethylsulfate group.

The polyoxyethylene alkyl ether sulfate salt of formula (I) is usually prepared by adding a prescribed number of moles of ethylene oxide to a long-chain alcohol in the presence of a catalyst to obtain a polyoxyethylene alkyl ether and then sulfating and neutralizing the ether by conventional procedures.

The mole number of added ethylene oxide units is broadly distributed in the thus-prepared polyoxyethylene alkyl ether sulfate salt, and the product contains a considerable amount of an alkyl sulfate salt to which ethylene oxide was not added at all. In the case of conventional products prepared by using an alkali catalyst, the alkyl sulfate salt is contained in an amount of about 20 to about 70 wt.%, although this proportion varies to some extent depending on the average mole number of added ethylene oxide units.

In the polyoxyethylene alkyl ether sulfate salt of the formula (I) that is used in the present invention, the content of such alkyl sulfate salt must be not higher than 5% by weight. If this content exceeds 5% by weight, the cationic surface active agent used in the present invention cannot be dissolved to form a transparent solution, and precipitation of crystals occurs at low temperature. It is also necessary that the average mole number of added ethylene oxide should be in the range of from 1 to 5 in the polyoxyethylene alkyl ether sulfate salt used in the present invention. If the average mole number exceeds 5, the foaming property is drastically lowered and the basic property required of a shampoo is lost.

The cationic surface active agent of the formula (II) that is used in the present invention has a higher water-solubility and a higher hair-softening effect than the cationic surface active agents customarily used for hair rinses.

The shampoo composition of the present invention, if desired, may further contain the conventional amounts of other components customarily incorporated in conventional shampoos, such as a higher fatty acid alkanolamide (ordinarily 1 to 8% by weight), a non-ionic surface active agent (0.1 to 5% by weight) such as polyoxyethylene alkyl ether, sodium chloride (0.1 to 3% by weight), an oil component (0.1 to 2% by weight) such as a higher alcohol or isopropyl myristate, an antioxidant, a chelating agent, an ultraviolet absorber, a fungicide, a preservative, a perfume and a dye.

The present invention will now be described in detail by reference to the following experiments and illustrative examples.

EXPERIMENT 1

Various cationic surface active agents were tested with respect to their hair-softening effect.

A human hair bundle having a diameter of 2 cm and a length of 15 cm was dipped for 1 minute in a 1.0% aqueous solution of a cationic surface active agent. The hair bundle was taken out from the aqueous solution and the suppleness was evaluated according to the organoleptic test method. The results shown in Table 1 were obtained. In Table 1, the symbols have the following meanings:

◎: very supple
○: supple
Δ: slightly supple
X: not supple at all

Table 1

| Sample No. | Cationic Surface Active Agent | Evaluation |
|---|---|---|
| (1) | $[C_{18}H_{37}\text{-}N(CH_3)_2\text{-}C_{18}H_{37}]^+ Cl^-$ | ◎ |
| (2) | $[C_{18}H_{37}\text{-}N(CH_3)_3]^+ Cl^-$ | ◎ |
| (3) | $[C_{18}H_{37}\text{-}N(CH_3)_2\text{-}CH_2\text{-}C_6H_5]^+ Cl^-$ | ○ |
| (4) | $[C_{18}H_{37}\text{-}N(CH_3)((CH_2CH_2O)_nH)((CH_2CH_2O)_mH)]^+ Cl^-$ | X |
| (5) | $[C_{18}H_{37}\text{-}N(CH_3)_2\text{-}CH_2CH_2CH_2\text{-}N(CH_3)_2\text{-}CH_3]^{++} 2Cl^-$ | Δ |

Table 1-continued

| Sample No. | Cationic Surface Active Agent | Evaluation |
|---|---|---|
| (6) | $[C_{12}H_{25}\text{-}N(CH_3)_2\text{-}CH_2\text{-}C_6H_5]^+ Cl^-$ | X |

Among the samples shown in Table 1, samples 1, 2 and 3 are excellent in the hair-softening effect. Sample 1 is substantially water-insoluble and it cannot be used for preparing a transparent shampoo. Samples 4, 5, 6 and 7 can be incorporated into conventional shampoos without damaging the transparency, but they are much inferior in the hair-softening effect and the intended purpose of the present invention cannot be attained by using them. Samples 2 and 3 have a good hair-softening effect and are substantially water-soluble. However, it is difficult to incorporate them into conventional anionic surface active agent bases without damaging the transparency and causing precipitation of crystals in the resulting compositions at room temperature.

In order to incorporate a cationic surface active agent such as sample 2 or 3 into an anionic surface active agent-based shampoo and obtain a transparent liquid shampoo composition capable of giving a good supple touch to washed hair, it is critical to use a special anionic surface active agent as specified in the present invention.

EXPERIMENT 2

The compatibility of the cationic surface active agent 2 of Experiment 1, which is included in the scope of the present invention, with various anionic surface active agents was examined.

The cationic surface active agent 2 was dissolved with heating, in an amount of 1 wt.%, into a 20% aqueous solution of an anionic surface active agent indicated below. The solution was allowed to stand still for 3 days in a constant temperature vessel maintained at −5° C and the transparency was examined. The results shown in Table 2 were obtained.

Table 2

| Anionic Surface Active Agent | Transparency |
|---|---|
| Sodium polyoxyethylene lauryl ether sulfate (the average mole number of added ethylene oxide units being 3.3 and the n = 0 content being 32 wt. %) | opaque crystals precipitated |
| Sodium polyoxyethylene lauryl ether sulfate (the average mole number of added ethylene oxide units being 3.8 and the n = 0 content being 3.0 wt. %) | transparent |
| Triethanolamine lauryl sulfate | opaque crystals precipitated |
| Triethanolamine laurate | opaque crystals precipitated |

EXAMPLE 1

| | |
|---|---|
| Sodium polyoxyethylene lauryl ether sulfate (the average mole number of added ethylene oxide units being 3.5 and the n = 0 content being 4 wt. %) | 20% by weight |
| Stearyltrimethyl ammonium chloride | 1.0% by weight |
| Coconut fatty acid diethanolamide | 4.5% by weight |
| Perfume and dye | minor amounts |
| Deionized water | 74.5% by weight |

The above components were mixed and heated to form a solution. The solution was cooled and filled in a bottle. The thus-formed shampoo was transparent even after it had been stored for 1 month at −5° C. Hair washed by using this shampoo was very soft and supple.

EXAMPLE 2

| | |
|---|---|
| Sodium polyoxyethylene lauryl ether sulfate (the average mole number of added ethylene oxide units being 2.5 and the n = 0 content being 5.0 wt. %) | 15.0% by weight |
| Stearyldimethyl benzyl ammonium chloride | 0.5% by weight |
| Lauroyl diethanolamide | 5.0% by weight |
| Perfume and dye | minor amounts |
| Deionized water | 79.5% by weight |

The above-components were formed into a shampoo. The thus-formed shampoo was transparent even after it had been stored for 1 month at −5° C. Hair washed by using this shampoo was very soft and supple.

The embodiments of the invention in which an exclusive property or privilege is claimed are defined as follows:

1. A transparent liquid shampoo composition, consisting essentially of
   A. from about 10 to about 40 weight percent of an anionic surfactant having the formula $$R_1-O-(CH_2CH_2O)_nSO_3M$$

wherein $R_1$ is alkyl having from 10 to 18 carbon atoms, $n$ is the average number of added ethylene oxide units and is in the range of from one to 5, with the proviso that compound in which $n$ equals zero is from zero to 5 weight percent of the total weight of component A, and M is an alkali metal or an alkanolamine selected from the group consisting of mono-, di- and triethanolamine,
   B. from about 0.1 to about 5 weight percent of cationic surfactant having the formula

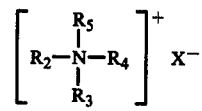

wherein $R_2$ is alkyl having 16 to 22 carbon atoms, $R_3$ and $R_4$ are methyl or ethyl, $R_5$ is methyl, ethyl or benzyl, and X is chloro, bromo, iodo or monoethylsulfate, and
   C. the balance is essentially water.

2. A shampoo composition according to claim 1 in which the amount of component A is from 13 to 25 weight percent, and the amount of component B is from 0.3 to 3 weight percent.

3. A shampoo composition according to claim 2 in which $R_1$ contains from 12 to 14 carbon atoms, $n$ is from 2 to 4 and the content of compound in which $n$ equals zero is less than 4 weight percent of the total weight of component A.

4. A shampoo composition according to claim 2 in which $R_3$, $R_4$ and $R_5$ are methyl.

5. A shampoo composition according to claim 1, containing from one to 8 weight percent of a higher fatty acid alkanolamide, or from 0.1 to 5 weight percent of a non-ionic surfactant, or from 0.1 to 3 weight percent of sodium chloride, or from 0.1 to 2 weight percent of a higher alcohol or isopropylmyristate, or combinations thereof.

* * * * *